United States Patent [19]

Krause

[11] Patent Number: 4,609,350

[45] Date of Patent: Sep. 2, 1986

[54] LINGUAL RETAINER AND METHODS OF MANUFACTURING AND BONDING SAME

[76] Inventor: Frank W. Krause, 20 Pittsfield St., Cranford, N.J. 07036

[21] Appl. No.: 690,035

[22] Filed: Jan. 9, 1985

[51] Int. Cl.⁴ .............................................. A61C 7/00
[52] U.S. Cl. ....................................... 433/7; 433/215; 433/24; 433/9
[58] Field of Search .......................... 433/7, 9, 24, 215

[56] References Cited

PUBLICATIONS

"Lingual Orthodontics: A Status Report, Part 5 Lingual Mechanotherapy", JCO, Feb., 1983, pp. 99–115.
"Lingual Orthodontics: A Status Report, Part 7A Case Reports–Non-Extraction Consolidation", JCO, May 1983, pp. 310–321.
"Catalog of Products and Services", of Professional Positioners, p. 14.
American Journal of Orthodontics, Apr. 1982, Publication, pp. 274 and 275.
American Journal of Orthodontics, Sep. 1979, Publication, p. 25.
Professional Positioners, brochure entilted "Orthodontic Laboratory Services".

*Primary Examiner*—Robert Peshock
*Attorney, Agent, or Firm*—Lerner, David, Littenberg, Krumholz & Mentlik

[57] ABSTRACT

A custom lingual retainer is construced by custom fitting a preformed base into the lingual fossa of a tooth. A wire, which extends beyond the tooth, is attached thereto. A custom lingual retainer so produced is bonded by applying a bonding adhesive to a surface of the metal base of the retainer and positioning the metal base in the lingual fossa of the tooth.

28 Claims, 6 Drawing Figures

FIG. 3
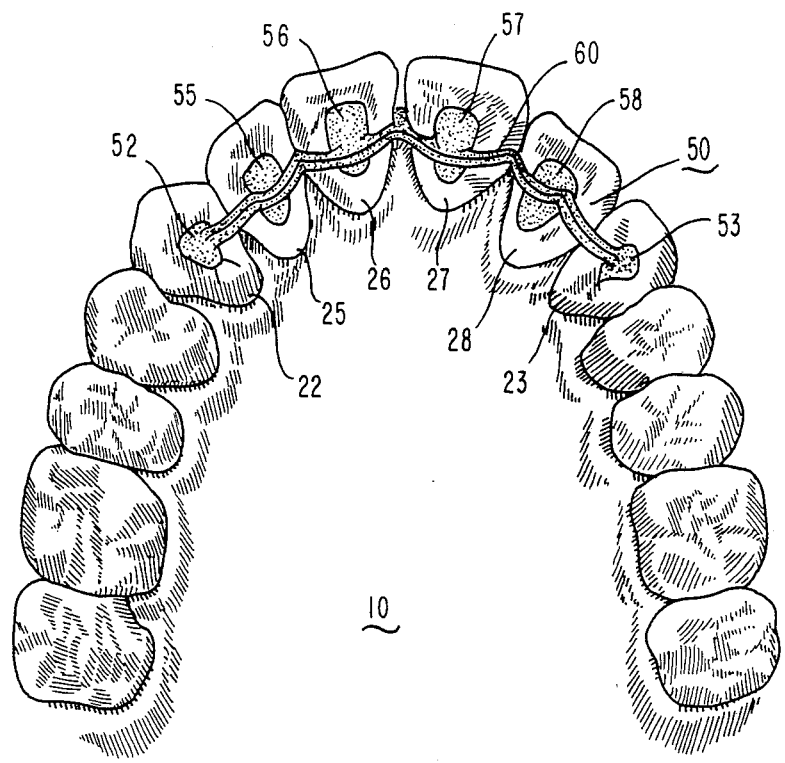
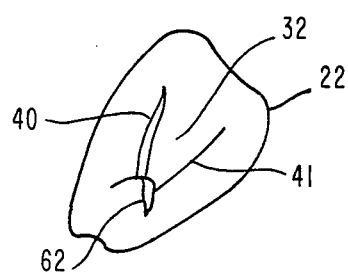
FIG. 4
FIG. 5
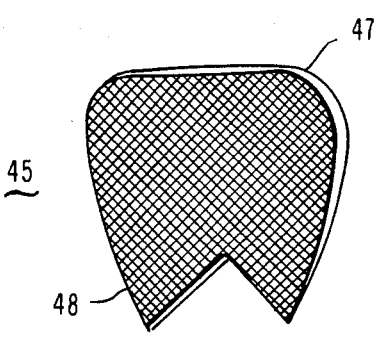

4,609,350

LINGUAL RETAINER AND METHODS OF MANUFACTURING AND BONDING SAME

BACKGROUND OF THE INVENTION

The present invention is related generally to orthodontic-dental appliances and more particularly to retainers intended to guide post-treatment settling processes.

Conventional retainers, such as the Hawley retainer, are often used for orthodontic purposes for the maxillary anterior teeth. This retainer is comprised of a metal wire positioned across the labial surface of the maxillary teeth and an acrylic portion positioned across the lingual surface of the maxillary teeth. This retainer is normally worn for a period of eighteen to twenty-four months and is commonly worn full-time for the first six months, one-half time for the second six months, and at night for the remainder of the time period. This retainer, however, suffers from several drawbacks including physical irritations and allergic reactions to the lingual acrylic portion of the retainer. Furthermore, because the retainer is removable, it is often lost, misplaced or damaged. Additionally, for cosmetic reasons, many patients refuse to wear the retainer or wear it for only a portion of the time necessary. Thus, it is desirable to minimize the time during which a patient must wear a Hawley retainer. Finally, some adult patients suffer from a loss of alveolar bone support and a Hawley retainer alone is not adequate for retention.

Once the teeth have been properly aligned by the orthodontic appliance, it is necessary to continue wearing the Hawley retainer at least a portion of the time such that the teeth do not relapse to the prior condition. Certain extreme pretreatment maxillary deficiencies such as crowding, spacing, rotation, palatally blocked lateral incisors, and muscle imbalance, require more secure, semipermanent retention than removable maxillary retainers provide. One solution is the bonding of a passive splint wire to the lingual surfaces of the maxillary anterior teeth with a plastic substance. However, this direct bonding process is often inaccurate, tedious and time-consuming and does not yield consistently reproducible results. Another solution is the bonding of a cuspid to cuspid lingual retainer which is preformed and available in graded sizes. Preformed lingual retainers, although they provide effective retention in the mandibular arch, have not been as successful in retaining maxillary anterior teeth. This is due to the fact that the strength of the retainer and accuracy of its position in the maxillary arch is much more demanding because of the irregular tooth morphology of maxillary incisors and the greater need to withstand mechanical occlusal stress. Also, since too few size increments are available, preformed anterior retainers are frequently too long or too short to fit accurately. Maxillary retainers that do not fit precisely lack resistance form and do not effectively permit occlusal forces to be dissapated in the teeth and periodontal structures. Consequently, the shearing forces applied more readily weaken the resin bond and lead to bond failure. Thus, although desirable, bonded retention of maxillary anterior teeth has remained difficult and has not gained wide acceptance.

SUMMARY OF THE INVENTION

The present invention is directed to a new custom lingual retainer and methods of manufacturing and bonding the lingual retainer. Typically, an impression is made of the teeth in order to prepare a model made of laboratory stone. In certain patients it may be necessary to prepare the lingual fossa of the incisors prior to taking the impression. This preparation may take the form of reducing the cingulum within the fossa and accenting the mesial and the distal ridge of the fossa. Once the fossa has been prepared, the impression of the teeth is taken and the laboratory model is produced.

Working with the laboratory model, a preformed bracket base or bonding pad is custom fit into the lingual fossa. A soft wire is positioned proximate to the base which is then connected to the soft wire by soldering. The soldering step allows solder to flow to the periphery of the base while maintaining the thickness of the soldered joint at a minimum. The custom lingual retainer of the present invention is thus constructed of a base custom fit to the lingual fossa of a tooth to be held by the retainer and has a soft wire connected thereto and extending therebeyond. The lingual retainer is constructed of a triangular steel member or a triangular member constructed of an etchable solderable alloy. The triangular steel member may have a steel mesh attached thereto. Where more than one base is used, the triangular bases are interconnected by soldering each of the bases to the soft rectangular wire.

After the retainer has been constructed, and while the retainer is still fitted to the laboratory model, the retainer and laboratory model are encapsulated in a material to produce a transfer tray. When the transfer tray is removed from the laboratory model it contains the custom-made retainer therein. The transfer tray is used for indirectly transfering the custom-made retainer to the patient's teeth.

The method of bonding the lingual retainer of the present invention comprises the steps of applying a bonding adhesive to a surface of a metal base or bonding pad of the retainer and positioning the metal base in the lingual fossa.

The present invention represents the first lingual retainer which takes advantage of the lingual fossa naturally occurring in anterior teeth to provide additional support for bonding the retainer. Because of this feature, mechanical occlusal stress which tends to break bonds and which is exerted against maxillary lingual retainers through direct occlusal contact or biting forces are successfully dissipated to the teeth and surrounding periodontal structures. The lingual retainer of the present invention suffers from none of the drawbacks of the Hawley retainer in that it has no acrylic which may cause allergic reations, is not removable and therefore cannot be lost, presents no cosmetic problems, and can be worn full time to provide excellent support to guide the post-treatment settling process. Additionally, the custom lingual retainer of the present invention permits flossing, can be prepared inexpensively and requires a minimum of chair time for bonding of same to the patient's teeth. These and other advantages and benefits of the present invention will become apparent from the description of a preferred embodiment hereinbelow.

BRIEF DESCRIPTION OF THE DRAWINGS

FIG. 3 is a lingual view of the maxillary teeth with a custom lingual retainer of the present invention bonded to the anterior teeth;

FIG. 4 illustrates the fossa and cingulum rest of a cuspid;

FIG. 5 is a perspective view of a notched metal base of the present invention.

DESCRIPTION OF THE PRESENT INVENTION

Figure 1:
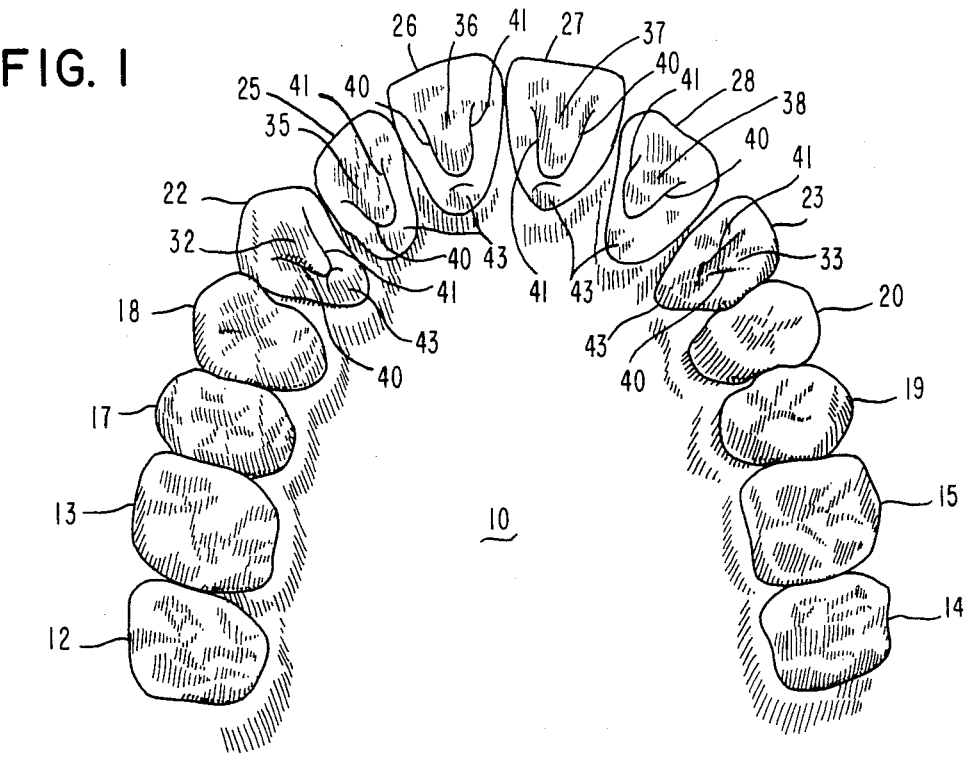
FIG. 1 is a lingual view of the maxillary teeth.

Illustrated in FIG. 1 is a lingual view of the maxillary teeth 10. In an adult the maxillary teeth 10 include four molars 12, 13, 14 and 15, four premolars or bicuspids 17, 18, 19, and 20, two canine or cuspids 22 and 23, and four incisors 25, 26, 27, and 28. The maxillary teeth are illustrated in FIG. 1 in their proper position. However, many adults suffer from maxillary deficiencies such as crowding, spacing, rotations, palatally blocked lateral incisors, and muscle imbalance which subsequent to orthodontic correction require stabilization with an orthodontic retainer. One such retainer is the Hawley retainer which is constructed of a metal wire positioned across the labial surface of the teeth and an acrylic portion positioned across the lingual surface of the teeth. This retainer is used after the teeth have been moved into their proper postion as illustrated in FIG. 1. However, for several reasons such as physical discomfort, allergic reactions, cosmetic reasons, or the like, patients typically desire to wear the Hawley retainer a minimum amount of time. Unfortunately, after the teeth have been brought into proper position as illustrated in FIG. 1, removal of the retainer may allow the teeth to relapse into the improper positions which existed before treatment due largely to the memory and elasticity of the supracrestal fibers. The retainer of the present invention is directed according to one aspect of the invention, to this post-treatment settling process such that the time during which the patient must wear the Hawley retainer is kept to a minimum while assuring that post-treatment settlement processes will not cause the teeth to relapse into the positions which existed prior to treatment. Selected cases may be retained with the present invention alone.

The present invention is for a custom lingual retainer which utilizes the morphology of the maxillary anterior teeth 22, 25, 26, 27, 28 and 23. The cuspid 22 has a fossa indicated by reference numeral 32 and the cuspid 23 has a fossa indicated by reference numeral 33. The fossa 32 and 33 are a generally V-shaped depression in the lingual surface of the cuspids 22 and 23 and are comprised of a distal ridge 40 and a mesial ridge 41. Each of the cuspids 22 and 23 also has an inverted V-shaped eminence 43, referred to as a cingulum, extending from the elastic interceptal fiber to the base of the V-shaped fossa 32, 33.

The incisor 25 has a fossa indicated by reference numeral 35, the incisor 26 has a fossa indicated by reference numeral 36, the incisor 27 has a fossa indicated by reference numeral 37, and the incisor 28 has a fossa represented by reference numeral 38. Each of the fossa 35–38, inclusive, is a generally U-shaped depression in the lingual surface of the incisor and is comprised of a distal ridge 40 and a mesial ridge 41. Each of the incisors 25–28, inclusive, also has a cingulum 43 extending from the elastic interceptal fiber to the base of the U-shaped fossa. The present invention utilizes the distal and mesial ridges of the fossa as well as the cingulum of each tooth to provide a secure anchorage for the base or bases of the custom lingual retainer.

Figure 2:
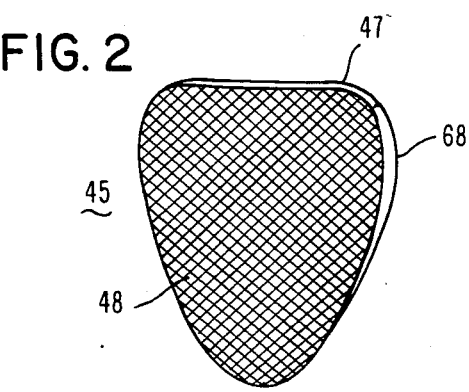
FIG. 2 is a perspective view of one type of metal base of the present invention.

Turning now to FIG. 2, a typical base or bonding pad (shown greatly enlarged) 45 used in the construction of the custom lingual retainer of the present invention is illustrated. The metal base 45 is constructed of a generally triangular shaped metal member 47 to which a generally triangular shaped wire mesh 48 has been attached. The metal member 47 is constructed of steel and can be stamped from a suitable sheet of steel to permit fabrication by mass production techniques. The wire mesh 48 is a steel mesh attached to one surface of the metal member 47. the wire mesh 48 is provided on the surface which is to be bonded to the lingual surface of the anterior teeth shown in FIG. 1 and provides an improved bonding surface. Such preformed bases are currently available from Unitek Corporation located at 2724 South Peck Road, Monrovia, Calif. 91016.

It is anticipated that with the advent of the development of superbonding adhesives, the metal base 45 may be used in the present invention without the wire mesh 48. Superbond adhesives interact chemically with the metal surface thus insuring a solid microscopic bond without requiring the rough surface provided by the wire mesh 48. One such superbond adhesive is Panavia-Ex, manufactured by J. Morita Co. located at 12 Galloway Avenue, Cockeysville, Md. 21030.

A still further type of metal base which may be used in conjunction with the present invention is constructed of an alloy and has the same general triangular shape as the member 45 shown in FIG. 2. The alloy chosen should have characteristics such that it can be mass produced by stamping, or othr mass production techniques, is solderable (for reasons which will be explained more fully hereinafter), and is etchable. Choosing an alloy which is etchable is desirable in that one surface of a metal base fabricated from an alloy will be etched according to well known etching techniques in order to produce a rough or scored surface to improve the bond between the metal base and the lingual surface of the incisors 25–28 illustrated in FIG. 1. It is anticipated that additional types of bases may be fabricated from new materials and new bonding adhesive developed which nonetheless fall within the teachings of the present invention.

Turning now to FIG. 3, a custom lingual retainer 50 is shown bonded to the cuspids 22 and 23 and incisors 25–28 of the maxillary teeth 10. The custom maxillary lingual retainer 50 is constructed of six bases, 52, 53, 55, 56, 57, and 58 similar to the base 45 shown in FIG. 2. Each of the bases is soldered to a soft steel rectangular wire 60.

The clinical procedures necessary to prepare the teeth prior to construction of the custom lingual retainer 50, the construction of the custom lingual retainer 50, and the bonding of the custom lingual retainer 50 to the cuspids 22 and 23 and incisors 25–28, inclusive, will now be described. After the maxillary anterior teeth shown in FIG. 1 have been ideally positioned and are esthetically detailed with all interproximal spaces closed, it is necessary to clinically examine the fossa 35–38 of each of the incisors 25–28. In certain patients it may be necessary to accent the distal ridge 40 and mesial ridge 41 by deepening the respective internal axial walls with small diameter round diamond stones to highlight the shape of the fossa. In certain patients it may also be necessary to reduce the incisal portion of the cingulum present in the bottom of the U-shaped fossa. Removal of any cingulum present in this portion of the fossa permits the creation of a cingulum rest continuous with the internal rounded axial line angles of the marginal ridges. Occlusal rests are commonly created on posterior teeth. However, in the present invention the cingulum or occlusal rest becomes a vital functional part of the resistance form resisting compressive forces while the marginal ridges resist shearing forces. Preparation of the fossa 35-38 typically requires the removal of approximately 0.1 mm of tooth enamel.

The preparation of the fossa 32 and 33 of the cuspids 22 and 23 is similar to the preparation of the fossa of the incisors. However, the cingulum of a cuspid is characteristically larger having a greater convex surface extending incisally into the fossa. Therefore, the cingulum rest 62 of the cuspid 22 shown in FIG. 4 is more conservatively prepared in the form of a peak or inverted "V". Bonding bases can be easily notched as shown in FIG. 5 to closely overlay the prepared cingulum rest forming a chevron. A cuspid occlusal rest thus prepared offers the additional advantage of protecting against shearing as well as compressive forces.

The lingual fossa and marginal ridges on cuspids characteristically are not as well defined as on incisors. Consequently, when the fitted bonding pads cannot be adequately protected by the bracing action of elevated-opposing marginal ridges, the introduction of the inverted "V" shape design of the occlusal rest assists in helping overcome the natural resistance form deficiency of the cuspid.

After the fossa of the teeth have been prepared, where necessary, an alginate impression of the teeth to be retained is taken in a rigid, well fitting tray. The impression must accurately reproduce all the teeth, particularly the lingual surfaces, including the fossa and gingival crest. Models should be poured immediately in laboratory stone. Normally, an orthodontically corrected occlusion will not have a deep overbite, making a wax bite and mandibular model unnecessary. Minimizing the time between taking the impression of the teeth and actually bonding the retainer to the teeth helps insure accurate seating of the retainer. Where an orthodontic appliance is removed and the maxillary anterior teeth are not stabilized by a passive archwire between impression taking and bonding of the retainer, even minimal tooth movement may block the transfer tray from seating accurately. For this reason, the maxillary anterior teeth may be temporarily stabilized by a vacuum-formed plastic splint for the time period between appliance removal and bonding of the custom lingual retainer.

Once the laboratory stone model of the teeth has been poured, bases 45, as shown in FIGS. 2 or 5, are custom fitted into the fossa of each of the teeth to be held by the retainer. The triangular shape and slightly rounded sides and corners of the bases conform well to the lingual anatomy of the incisors. The rolled elevations of the enveloping mesial and distal ridges as well as the cingulum rest provide a resistance form offering occlusal protection to the firmly seated triangular bases which reduces the chance of bond failure.

After the preformed bases 45 are custom fit into the fossa, a soft steel rectangular wire is positioned proximate to each of the bases and is hydro-flame soldered thereto. The soft steel rectangular wire may typically have a dimension of 0.018 inches by 0.022 inches. Round 0.020 spiral wound flex wire can be used in cases where maintenance of diastema closure is desired. The technician must flow the solder to the periphery of each base while keeping the bulk of the solder joint as thin as possible especially in the center of the base.

Figure 6:
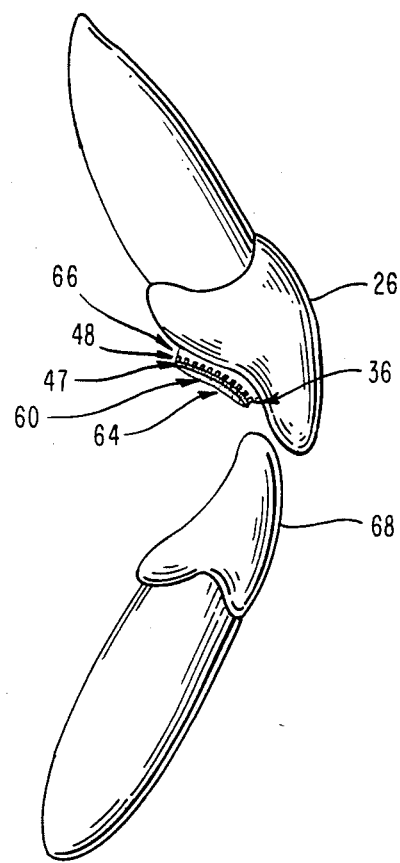
FIG. 6 is a profile of a maxillary incisor, carrying a metal base of the present invention, in occlusion with a mandibular incisor.

A custom lingual retainer constructed according to the present invention results in a smooth, low-profile retainer affording maximum patient comfort through minimal interference as illustrated in FIG. 6. In FIG. 6, a profile of a maxillary incisor 26 carrying a bonding base 45 is shown. The bonding base includes the metal member 47 which is paproximately 0.015 inches thick and the wire mesh 48 which is approximately 0.015 inches thick. The soft wire 60 and solder 64 are approximately 0.018 inches at their thickest point. A thin layer of adhesive 66 adds minimally to the profile of the retainer. The avoidance of direct occlusal contact with mandibular incisor 68 minimizes the possibility of bond failure.

The closely contoured, soft, interproximal wire 60 offers flexibility to absorb the physiological movement of adjacent teeth during mastication. The preformed bases are seated between the elevated distal and mesial ridges and buttressed against the cingulum rest to provide a resistance capable of converting unfavorable shearing forces into compressive forces that are more easily dissipated to the teeth and surrounding periodontal structures.

With the custom lingual retainer exactly fitted to the laboratory model of the teeth to be retained, the custom lingual retainer and laboratory model are encapsulated in a commercially available material to produce a transfer tray. One such material is a vinyl tray material known as 2 mm Bioplast available from Great Lakes Orthodontics located at 1550 Hertel Avenue, Buffalo, N.Y. 14216. When this transfer tray is removed from the laboratory model the custom lingual retainer is encapsulated therein in the exact position in which it will be located on the patient's teeth.

Before beginning the bonding procedure, the transfer tray should be trial fitted on the patient to insure complete and proper seating. A clear transfer tray permits visual verification of the seating. Once the transfer tray can be snapped into place with a secure fit, it should be removed and the exposed mesh bases should be cleaned with acetone or alcohol and the tray flushed with water.

A bonding material is placed on each of the metal bases. A bonding material containing a filler of 30,000 microns and larger is suitable for macroscopic bonding a custom lingual retainer having bases as shown in FIG. 2 to the lingual surface of the teeth. Where the metal bases of the custom lingual retainer are made of smooth steel and do not have a wire mesh bonding surface, microscopic superbonding adhesives should be used. Use of superbonding adhesives eliminates the need for the wire mesh 48 which reduces the profile projection of the retainer and allows for a more intimate fit of the base within the fossa. That enhances the resistance form of the fossa. The more intimate fit also produces a significantly stronger retentive bond. Where the metal bases of the custom lingual retainer are made of an alloy, if superbonding adhesives are not being used the alloy should be etched according to known procedures and an adhesive having a filler of 30,000 microns and less used for microscopic bonding.

When the transfer tray has been properly seated, it is imperative to hold it in place with a light but steady pressure from the lingual direction against the retainer for approximately three minutes to allow the bond to set. This will insure an intimate fit of the retainer, resulting in a uniformly thin mix of bonding adhesive that is conducive to maximum bond strength. The lingual pressure also causes the bonding adhesive to flow out beyond the edges of the base. This results in additional bonding between the edge 68 (shown in FIG. 2) of the base 45 and the mesial and distal ridges as well as the cingulum rest. The transfer tray should be left in place for a total of ten minutes. After the transfer tray has been removed, adhesive resin flash is removed with a scaler and tapered carbide bur and the teeth are checked for free contacts using dental floss.

It is not necessary, of course, to use the transfer tray method described above. Once the custom lingual retainer has been produced on the laboratory model, it may be directly transferred to the patient. However, indirect transfer of the custom lingual retainer is preferred because the oblique line of sight to the lingual surfaces makes it extremely difficult to exactly position the custom lingual retainer onto the lingual surfaces of the teeth. With acceptable technique and minimal chair time, indirect bonding of the custom lingual retainer eliminates most variables and reliably transfers the close tolerances of custom laboratory procedures to the mouth with routinely excellent results. By contrast, direct bonding transfer can be inaccurate and risky. Consequently, it is not recommended except when the original transfer tray has not been saved and there is a need for rebonding of the custom lingual retainer.

The custom lingual retainer of the present invention can be used in conjunction with a Hawley retainer or an acrylic adaptor available from Professional Positioners, P.O. Box 239, Racine, Wisc. 53401. When a custom lingual retainer and an adaptor are fabricated on the same model an effective means of retention for difficult cases can be realized. The custom lingual retainer serves to stabilize the incisors whereas the adaptor can be designed to control cuspid alignment and settling to close slight spaces throughout the arch and to maintain extraction site closure. A Hawley retainer and adaptor can be seated over a bonded custom lingual retainer without adjusting the closely approximating lingual acrylic of the adaptor. Standard Hawley retainers may also be constructed over the custom lingual retainer. If the maxillary teeth are already retained by a passive adaptor, it can serve as a stabilizing appliance. After indirect transfer of the custom lingual retainer the pointed tips of the adaptor's interproximal acrylic which are in contact with the soldered connecting wire of the custom lingual retainer may require slight reduction for positive seating of the adaptor.

The combination of the bonded custom lingual retainer and removable retainer may be especially desirable for the cosmetically concious patient or the patient experiencing difficulty in wearing a removable retainer during the day. A rapid transition from full-time to night-time wear of the removable retainer can be made without concern about incisor relapse. Some selected cases may be retained with the present invention alone.

Cuspids can be included in the custom lingual retainer when it is necessary to maintain their alignment and rotational correction. Normally, however, the inherent anchorage value of four splinted incisors will exert a stablizing influence on the cuspids. Ideally, the cuspids should be permitted to erupt and be allowed the freedom of adjustment into occlusion.

If a six-unit custom lingual retainer is bonded, it is recommended that the lower cuspids be allowed that freedom of adjustment against the fixed upper occlusion. A fixed lower banded retainer supported on the bicuspids is well accepted by the patient and will permit cuspid adjustment.

Although the present invention is discussed in terms of a custom lingual retainer fitted to the maxillary anterior teeth, it should be noted that the present invention may also be used on mandibular anterior teeth. Although a lingual retainer on the mandibular anterior teeth is not subject to occlusion and accordingly does not present the same problems due to close tolerances, the extremely short chair time (approximately ten minutes in a normal case) coupled with the low cost and ease of fabricating the custom lingual retainer of the present invention may make it desirable to use the present invention on mandibular anterior teeth as well. Additionally, bond failure on mandibular cuspids is not a contraindication.

While the present invention has been described in connection with an exemplary embodiment thereof, it will be understood that many modifications and variations will be readily apparent to those of ordinary skill in the art. This application and the following claims are intended to cover those modifications and variations.

What I claim is:

1. A method of bonding a custom lingual retainer comprising the steps of:
   accenting the mesial and distal ridges of the lingual fossa of a tooth by creating deeper internal rounded axial line angles.
   modifying the cingulum within the lingual fossa to form a cingulum rest.
   applying a bonding adhesive to a surface of a base of said retainer;
   attaching a wire to said base, said wire extending beyond said base; and
   positioning said base in the lingual fossa of the tooth.

2. The method according to claim 1 wherein the internal rounded axial line angles form a continuous U-shape on an incisor;

3. The method according to claim 1 wherein the internal rounded axial line angles form a continuous W-shape on a cuspid.

4. The method according to claim 1 wherein the step of positioning said base includes direct positioning of said base in the lingual fossa of said tooth.

5. The method according to claim 1 wherein the step of positioning said base includes indirect positioning of said base in the lingual fossa of said tooth.

6. The method according to claim 5 wherein the step of indirect positioning includes positioning a transfer tray carrying the retainer onto said tooth, holding said transfer tray in place with steady pressure, and removing said transfer tray.

7. The method according to claim 1 additionally comprising the step of etching said surface of said metal base prior to applying said bonding adhesive.

8. The method according to claim 1 wherein said applying step includes applying a superbond adhesive to said surface.

9. The method according to claim 1, wherein said custom lingual retainer is bonded after the tooth has been orthodontically corrected.

10. A method of making a custom lingual retainer comprising the steps of:
    accenting the mesial and distal ridges of the lingual fossa of a tooth by creating deeper internal rounded axial line angles, modifying the cingulum within the lingual fossa to form a cingulum rest.

custom fitting a preformed base into the lingual fossa of the tooth; and attaching a wire to said custom fitted base, said wire extending beyond said base.

11. The method according to claim 10 wherein the directly attaching step includes soldering said wire to said base and flowing the solder to the periphery of said base.

12. The method according to claim 11 wherein the soldering step includes minimizing the thickness of the soldered joint.

13. The method according to claim 10 wherein the step of custom fitting includes custom fitting said preformed base to a model of the tooth.

14. The method according to claim 13 additionally comprising the step of encapsulating said retainer when fitted to said model of said tooth to form a transfer tray.

15. The method according to claim 14 wherein said encapsulating step includes encapsulating said retainer with a transparent material.

16. The method according to claim 10 additionally comprising the step of etching the surface of said preformed base.

17. The method according to claim 10 wherein the step of custom fitting includes custom fitting a preformed base into the lingual fossa of each tooth to be held by said retainer and additionally comprising the step of interconnecting each of said bases with said soft wire.

18. A custom lingual retainer comprising:

a pair of bases adapted to be custom fit into an accented lingual fossa of a pair of spaced-apart teeth, said teeth accented by accenting the mesial and distal ridges of the lingual fossa of a tooth by creating deeper internal rounded axial line angles and modifying the cingulum within the lingual fossa to form a cingulum rest; and wire means directly connected to and extending between said pair of bases, said wire means comprising a wire of soft material adapted to absorb the physiological movement of adjacent teeth during mastication.

19. The custom lingual retainer according to claim 18 wherein said base is soldered to said wire and wherein the solder extends to the periphery of said base.

20. The custom lingual retainer according to claim 19 wherein the soldered joint is of minimal thickness.

21. The custom lingual retainer according to claim 18 wherein the base includes a triangular steel member.

22. The custom lingual retainer according to claim 21 additionally comprising a triangular steel mesh attached to said steel member.

23. The custom lingual retainer according to claim 18 wherein the base includes a triangular member made of an etchable alloy.

24. The custom lingual retainer according to claim 18 wherein said wire includes a soft rectangular wire approximately 0.022 inches wide and 0.018 inches thick.

25. The custom lingual retainer according to claim 18 wherein said wire includes a round spiral flex wire approximately 0.020 inches in diameter.

26. The custom lingual retainer according to claim 18 additionally comprising a second base adapted to be custom fit to the lingual fossa of a tooth to be held by said retainer, and wherein said wire interconnects said bases.

27. The custom lingual retainer according to claim 18, wherein said base includes a base having an inverted V-shaped portion.

28. The custom lingual retainer according to claim 18, wherein said base is adapted to be custom fit into the lingual fossa of a tooth after the tooth has been orthodontically corrected.

* * * * *

UNITED STATES PATENT AND TRADEMARK OFFICE
CERTIFICATE OF CORRECTION

PATENT NO. : 4,609,350

DATED : September 2, 1986

INVENTOR(S) : Frank W. Krause

It is certified that error appears in the above-identified patent and that said Letters Patent is hereby corrected as shown below:

In the Abstract:

line 1, change "construced" to --constructed--.

Column 4, line 34, change "othr" to --other--.

Column 6, line 11, change "paproximately" to --approximately--.

In the Claims:

Claim 7, line 2, delete "metal".

Signed and Sealed this
Sixth Day of January, 1987

Attest:

DONALD J. QUIGG

Attesting Officer      Commissioner of Patents and Trademarks